United States Patent [19]

Eguchi et al.

[11] Patent Number: 4,929,551

[45] Date of Patent: May 29, 1990

[54] PROCESS FOR PRODUCING L(−)-TETRAHYDROFOLIC ACID

[75] Inventors: Tamotsu Eguchi; Takashi Oshiro, both of Machida; Yukihiro Kuge, Osakasayama; Kenichi Mochida, Hiratsuka; Takayuki Uwajima, Machida, all of Japan

[73] Assignee: Kyowa Hakko Kogyo Co., Ltd., Tokyo, Japan

[21] Appl. No.: 393,795

[22] Filed: Aug. 15, 1989

[30] Foreign Application Priority Data

Aug. 30, 1988 [JP] Japan .................... 63-216045

[51] Int. Cl.$^5$ .................... C12P 13/04; C12N 9/06
[52] U.S. Cl. .................... 435/106; 435/119; 435/177; 435/191; 435/252.33; 435/280; 435/320; 435/814; 435/849
[58] Field of Search ............... 435/106, 280, 191, 119, 435/177, 814, 320, 252.33, 849

[56] References Cited

FOREIGN PATENT DOCUMENTS 0266042  5/1988  European Pat. Off. .
0128895  of 1986  Japan .

OTHER PUBLICATIONS

Biotech Abs 89-15096 Ottolina et al "Biochim Biophys Acta" (1989) 998, 2, 173-178.
Chem Abs 103, 174553(21) Charlton et al "J. Chem Soc" (7) pp. 1349-1353 (1985).
J. Medicinal Chemistry, Temple, Jr. C., et al. "Preparation and Purification of L-(±)-5-Formyl-5,6,7,8-tetrahydrofolic Acid," vol. 22, No. 6, p. 731 (1979).
Tetrahedron, Rees, L., et al. "Asymmetric Reduction of Dihydrofolate Using Dihydrofolate Reductase and Chiral Boron-Containing Compounds," vol. 42, No. 1, p. 117 (1986).
Methods in Enzymology, Reyes, P., et al., "Dihydrofolate Reductase: A Coupled Radiometric Assay," vol. 122. p. 360 (1986).

*Primary Examiner*—Herbert J. Lilling
*Attorney, Agent, or Firm*—Fitzpatrick, Cella, Harper & Scinto

[57] ABSTRACT

The invention relates to a process for producing L(−)-tetrahydrofolic acid which comprises allowing dihydrofolate reductase to act upon dihydrofolic acid in the presence of (1) NADP or NADPH, and (2) glucose and glucose dehydrogenase. L(−)-tetrahydrofolic acid is useful as the intermediate for L(−)-leucovarin.

7 Claims, No Drawings

PROCESS FOR PRODUCING L(−)-TETRAHYDROFOLIC ACID

BACKGROUND OF THE INVENTION

This invention relates to a process for producing L(−)-tetrahydrofolic acid which is a substance used as the starting material for the preparation of L(−)-leucovorin and for other purposes. L(−)-leucovorin is a useful medicament known to have an action of preventing pernicious anemia caused by administration of folic acid antagonists, such as methotrexate, and an action of enhancing the therapeutical effect of 5-fluorouracil, an anti-tumor agent.

The processes for producing L(−)-tetrahydrofolic acid may fall into two main groups: the chemical method and the enzymatic method.

As examples of the chemical method, are known a process in which folic acid is reduced with $NaBH_4$ in an aqueous solution and L(±)-tetrahydrofolic acid thus formed is resolved under an acidic condition [Journal of Medicinal Chemistry, 22, 731 (1979)]; and a process comprising attaching a chiral auxiliary group at either N-5 or N-10 of a mixture of 6R and 6S diastereoisomers of tetrahydrofolic acid, separating the new diastereoisomers, recovering the desired new diastereoisomer (6R or 6S) corresponding to the desired (6R or 6S) diastereoisomer, and converting the substantially pure new diastereoisomer recovered into the corresponding diastereoisomer (EP-A-0266042).

When producing L(−)-tetrahydrofolic acid from folic acid by the chemical method, L(±)-tetrahydrofolic acid is inevitably formed as a byproduct; hence, a step of optical resolution is indispensable to obtain pure L(−)-tetrahydrofolic acid, which results at a low production yield.

As an example of the enzymatic method, is known a process in which dihydrofolate reductase is allowed to act upon dihydrofolic acid in the presence of coenzyme NADPH [Tetrahedron, 42, 117 (1986)].

Reduction of one mole of dihydrofolic acid with dihydrofolate reductase is generally accompanied by oxidation of one mole of NADPH into one mole of NADP. NADPH is an expensive compound, and an enzymatic system to regenerate NADPH by reduction of NADP (hereinafter referred to as an NADPH-regenerating system) is frequently used in order to diminish the manufacturing cost.

Heretofore, there have been known NADPH-regenerating systems using isocitrate dehydrogenase or glucose-6-phosphate dehydrogenase [Tetrahedron, 42, 117 (1986)], malate dehydrogenase (Japanese Published Unexamined Patent Application No. 128895/1986), and 6-phosphogluconate dehydrogenase [Methods in Enzymology, 122, 360 (1986)].

When isocitrate dehydrogenase is used in NADPH-regenerating system in the enzymatic process for producing L(−)-tetrahydrofolic acid by the action of dihydrofolate dehydrogenase upon dihydrofolic acid, isocitric acid used as substrate is an expensive compound, the reaction takes a long time and the production yield is low. When glucose-6phosphate dehydrogenase is used in the NADPH-regenerating system, glucose-6-phosphate used as substrate is an expensive compound, creatine kinase or acetate kinase must be used in the reaction system to supply glucose-6-phosphate used as substrate, the reaction takes a long time and the production yield is low. When malate dehydrogenase is used in the NADPH-regenerating system, dihydrofolate reductase is allowed to act upon dihydrofolic acid at such a low concentration as 2.9 mM, which results in only a small amount of L(−)-tetrahydrofolic acid. In addition, much NADPH has to be used as compared with the amount of dihydrofolic acid; hence, this is not an efficient process. When 6-phosphogluconate dehydrogenase is used in the NADPH-regenerating system, 6-phosphogluconic acid used as substrate is an expensive compound, the concentration of dihydrofolic acid is low, and much NADPH has to be used as compared with the amount of dihydrofolic acid; hence, this is not an efficient process.

As a result of intensive studies to develop an efficient industrial process for producing L(−)-tetrahydrofolic acid (hereinafter referred to as tetrahydrofolic acid) at a low cost, we have found that use of glucose dehydrogenase in the NADPH-regenerating system in the enzymatic process allows dihydrofolate reductase to act upon dihydrofolic acid at a high concentration in the presence of a small amount of NADPH, thereby producing tetrahydrofolic acid at high efficiency.

SUMMARY OF THE INVENTION

The present invention provides a process for producing L(−)-tetrahydrofolic acid which comprises allowing dihydrofolate reductase to act upon dihydrofolic acid in the presence of (1) NADP or NADPH, (2) glucose and (3) glucose dehydrogenase in an aqueous solution; accumulating L(−)-tetrahydrofolic acid in the aqueous solution; and recovering the L(−)-tetrahydrofolic acid therefrom.

DETAILED DESCRIPTION OF THE INVENTION

The dihydrofolate reductase used in the process of the present invention may be a highly purified enzyme preparation, a roughly purified enzyme preparation, or a dihydrofolate reductase-containing substance, such as microbial cells having dihydrofolate reductase activity and a treated product thereof. As the microbial cells having dihydrofolate reductase activity, an *Escherichia coli* strain carrying the plasmid described in JP-A-69990/87 is preferably used. As the treated microbial cells, mention may be made of dried products, surfactant-treated products, enzyme-treated products, ultrasonically treated products, mechanically disrupted products, solvent-treated products, protein fractions of cells, and immobilized products of cells or treated cells.

As the glucose dehydrogenase used in the process of the present invention, any of a highly purified preparation, a roughly purified preparation and a glucose dehydrogenase-containing substance such as treated products of microbial cells having glucose dehydrogenase activity may be used, so long as it is capable of reducing NADP into NADPH. As the enzyme source, mention may be made of microorganisms belonging to the genus Acetobacter, Bacterium, Gluconobacter, Pseudomonas or Xanthomonas, and livers of higher animals. Highly purified enzyme preparations may be obtained, for example, by mechanically disrupting the cells of a microorganism capable of producing the enzyme and purifying the resulting solution by means of salting-out, adsorption chromatography, ion-exchange chromatography or affinity chromatography.

With the dihydrofolate reductase and the glucose dehydrogenase, it is possible to immobilize the highly or roughly purified preparation thereof by a carrier (e.g., alginic acid) by a known technique, and use the immobilized preparation repeatedly.

The reaction of dihydrofolate reductase with dihydrofolic acid is effected by adding dihydrofolate reductase and glucose dehydrogenase to water, a phosphate buffer or a Tris-HCl buffer which contains dihydrofolic acid, glucose and NADPH, and holding the resulting mixture at a temperature in the range of 20° to 40° C., preferably 28° to 32° C., at a pH is the range of 5 to 8, preferably 6 to 7. It is preferable that the reaction be carried out with stirring while blowing an inert gas such as nitrogen and argon into the reaction mixture to keep oxygen out of the reaction system.

The concentration of dihydrofolic acid in the reaction system is in the range of 10 to 300 mM, preferably 30 to 200 mM, that of glucose is in the range of 10 to 1,000 mM, preferably 50 to 300 mM, and that of NADPH is in the range of 0.02 to 10 mM, preferably 0.5 to 5 mM. NADP may be used in place of NADPH.

The concentration of dihydrofolate reductase and that of glucose dehydrogenase in the reaction solution are both in the range of 1 to 20 U/ml, preferably 3 to 10 U/ml.

The activity of dihydrofolate reductase is determined at pH 7.4 according to the method described in Biochemistry, 14, 5267 (1975). The activity of glucose dehydrogenase is expressed by defining the amount that reduces 1 μmole of glucose in one minute at 30° C. in 100 mM phosphate buffer (pH 7.0) as one unit (1 U).

As the dihydrofolic acid in the reaction system is reduced by the action of dihydrofolate reductase, tetrahydrofolic acid is accumulated in the reaction solution. The change in the amount of dihydrofolic acid is monitored, and the accumulated tetrahydrofolic acid is recovered at the time when all the dihydrofolic acid is consumed. The reaction time is usually 0.5 to 18 hours.

It is also possible to determine the amount of dihydrofolic acid by analyzing consumed glucose in place of dihydrofolic acid.

Quantitative analysis of dihydrofolic acid is carried out according to the method described in Methods in Enzymology, 181, 605 (1971), and glucose is quantitatively analyzed by the use of Glucose Analyzer GL-101 (product of Mitsubishi Kasei Corporation).

Tetrahydrofolic acid formed, which is an unstable compound, is analyzed after being converted to its methenyl derivative according to the method described in Journal of Chromatography, 140, 114 (1977).

Tetrahydrofolic acid formed may be recovered according to the method described in Journal of Medicinal Chemistry, 22, 731 (1979) and converted to L-leucovorin.

The following examples will further illustrate the invention.

EXAMPLE 1

To 100 ml of an aqueous solution containing 52 mM dihydrofolic acid, 61 mM glucose and 1.0 mM NADPH adjusted to pH 6.85 with NaOH, were added 5.7 U/ml dihydrofolate reductase and 5.6 U/ml glucose dehydrogenase. The reaction was carried out at 30° C. with stirring while blowing nitrogen gas, and the changes in the concentrations of dihydrofolic acid and glucose were monitored. During the whole course of reaction, the pH was maintained in the range of 6.8 to 7.0 by addition of 3N-NaOH. Two hours and forty minutes after the start of reaction, when all the dihydrofolic acid was converted to tetrahydrofolic acid, 1.9 g of sodium ascorbate was added, and stirring was further continued for 20 minutes. After lowering pH of the reaction mixture of 3.55 by addition of hydrochloric acid, the mixture was stirred for 2 hours under ice cooling. A precipitate of tetrahydrofolic acid separated out, and the precipitate was collected by filtration and washed with water. To the precipitate thus obtained, were added 40 ml of formic acid and 8 ml of trifluoroacetic acid, and the mixture was allowed to stand at room temperature for 17 hours under a nitrogen gas stream. The reaction mixture was concentrated under reduced pressure, 60 ml of 0.5 N-HCl was added to the concentrate, and the resulting mixture was allowed to stand overnight with stirring. A precipitate separated out, and the precipitate was collected by filtration and dried, giving 2.43 g of methenyl derivative of tetrahydrofolic acid (yield: 71%).

EXPERIMENT

Methenyl derivative of tetrahydrofolic acid obtained in Example 1 (2.43 g) was added to 58 ml of hot water, and the mixture was heated for 5.5 hours in an oil bath of 120° C. while maintaining the pH in the range of 5.6 to 6.9 by addition of NaOH. At the end of reaction, 1.2 g of anhydrous calcium chloride and 11 ml of ethanol were added, and stirring was carried out for one hour.

A precipitate separated out, and the precipitate was filtered off. 400 ml of ethanol was dropwise added to the filtrate under cooling over a period of one hour. A precipitate separated out, and the precipitate was collected by filtration and dried, giving 2.21 g of L(−)-leucovorin.

Its purity, when measured by HPLC, was 100%, the yield from dihydrofolic acid was 65%, and its optical purity was 99.9%. The final product was identified as L(−)-leucovorin by NMR and TLC.

What is claimed is:

1. A process for producing L(−)-tetrahydrofolic acid which comprises allowing dihydrofolate reductase to act upon dihydrofolic acid in the presence of (1) NADP or NADPH, (2) glucose and (3) glucose dehydrogenase in an aqueous solution; accumulating L(−)-tetrahydrofolic acid in the aqueous solution; and recovering the L(−)-tetrahydrofolic acid therefrom.

2. The process according to claim 1, wherein the dihydrofolate reductase and the glucose dehydrogenase are used in the form of a roughly purified enzyme preparation, a highly purified enzyme preparation, said enzyme-containing substance or an immobilized products thereof.

3. The process according to claim 1, wherein the glucose dehydrogenase originates from microorganisms belonging to the genus Acetobacter, Bacterium, Gluconobacter, Pseudomonas or Xanthomonas, or livers of higher animals.

4. The process according to claim 1, wherein the aqueous solution is selected from the group consisting of water and a buffer.

5. The process according to claim 1, wherein the concentration of dihydrofolic acid and that of NADP or NADPH are in the range of 10 to 300 mM and 0.02 to 10 mM, respectively.

6. The process according to claim 1, wherein the concentration of dihydrofolate reductase and that of glucose dehydrogenase are both in the range of 1 to 20 U/ml.

7. The process according to claim 1, wherein the reduction reaction is carried out at 20° to 40° C., at a pH of 5 to 8 for a period of time of 0.5 to 18 hours.

* * * * *